United States Patent [19]

Görlitzer et al.

[11] Patent Number: 4,647,568
[45] Date of Patent: Mar. 3, 1987

[54] CIRCULATION-ACTIVE HYDROXY-TETRA-HYDROPYRIDINELACTONES

[75] Inventors: Klaus Görlitzer; Ulrich Bartke, both of Berlin; Siegfried Goldmann, Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 673,296

[22] Filed: Nov. 20, 1984

[30] Foreign Application Priority Data

Dec. 2, 1983 [DE] Fed. Rep. of Germany ....... 3343658

[51] Int. Cl.$^4$ ............... C07D 491/048; A61K 31/455; A61K 31/695; A61K 31/535
[52] U.S. Cl. .................................. 514/302; 546/14; 546/116; 546/256; 544/127; 514/63; 514/232; 514/236
[58] Field of Search ............... 546/116, 14; 514/302, 514/236; 544/127

[56] References Cited

U.S. PATENT DOCUMENTS 4,145,432 3/1979 Sato ..................... 546/116
4,211,872 7/1980 Schmidt et al. ........ 546/116
4,532,248 7/1985 Frankowiak et al. ..... 514/302

Primary Examiner—Henry R. Jiles
Assistant Examiner—Dale A. Bjorkman
Attorney, Agent, or Firm—Sprung Horn Kramer & Woods

[57] ABSTRACT

Hydroxytetrahydropyridinelactones of the formula

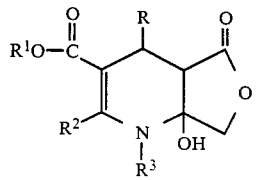

in which

R represents a phenyl, naphthyl, thienyl, furyl, pyryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, thionaphthenyl, isothionaphthenyl, chromonyl, thiochromonyl, chromenyl, thiochromenyl, benzoxadiazolyl or benzthiadiazolyl radical, and the stated radicals may carry 1 to 3 identical or different substituents from the group comprising $C_1$–$C_{20}$-alkyl, $C_2$–$C_{20}$-alkenyl, $C_2$–$C_{20}$-alkinyl, $C_1$–$C_{20}$-alkoxy, fluorine, chlorine, bromine, iodine, trifluoromethyl, monofluoro-$C_1$–$C_{10}$-alkoxy, polyfluoro-$C_1$–$C_{10}$-alkoxy, hydroxyl, amino, mono-$C_1$–$C_{10}$-alkylamino, di-$C_1$–$C_{10}$-alkylamino, nitro, cyano, azido, carboxyl, carb-$C_1$–$C_{10}$-alkoxy, carboxamido, sulphonamido, $SO_m$-alkyl (m=0 to 2, 1 to 20 C atoms), phenyl, benzyl, benzyloxy or benzylthio, it being possible for the 4 last-mentioned substituents to carry 1 to 3 radicals from the group comprising $C_1$–$C_5$-alkyl, $C_1$–$C_5$-alkoxy, $C_1$–$C_5$-alkylthio, fluorine, chlorine, bromine, iodine, cyano, nitro, azido, hydroxyl, trifluoromethyl, amino, $C_1$–$C_6$-alkylamino or di-$C_1$–$C_6$-alkylamino, $R^1$ represents a straight-chain, branched or cyclic saturated or unsaturated hydrocarbon radical which has 1–20 C atoms, may be interrupted in the chain by 1 or 2 oxygen or sulphur atoms and may be optionally substituted by one or more fluorine atoms, $NO_2$, $C_3$–$C_{12}$-trialkyl-silyl, hydroxyl, chlorine, bromine, iodine or cyano, $R^2$ represents hydrogen, —$NH_2$, —CHO, cyano, —$CH_2OH$ or a straight-chain or branched saturated or unsaturated hydrocarbon radical having 1 to 8 C atoms, $R^3$ represents hydrogen or a straight-chain or branched $C_1$–$C_{10}$-alkyl radical which may be interrupted in the alkyl chain by one or two oxygen atoms and may be optionally substituted by fluorine, chlorine, bromine, iodine, —CN, —$NH_2$, —OH or morpholino, which can be used as cardiotonics for improving the contractility of the heart. Moveover, they increase the flow of $Ca^{++}$ into the cells and can therefore be employed as antihypotonics, for lowering the blood sugar level, for reducing the swelling of mucous membranes and for influencing the salt balance and/or fluid balance.

10 Claims, No Drawings

CIRCULATION-ACTIVE HYDROXY-TETRA-HYDROPYRIDINELACTONES

The present invention relates to new 2-hydroxy-1,2,3,4-tetrahydropyridinelactones, i.e., hexahydrofuro-[3,4-b]pyridine derivatives, a process for their preparation and their use in medicaments, in particular in medicaments which influence the circulation.

The new compounds are characterized by the following formula (I):

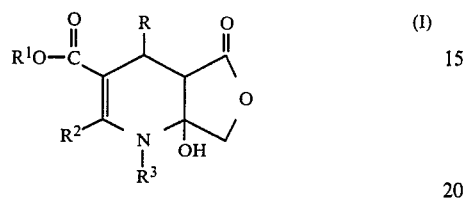

in which

R represents a phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, thionaphthenyl, isothionaphthenyl, chromonyl, thiochromonyl, chromenyl, thiochromenyl, benzoxadiazolyl or benzthiadiazolyl radical, and the stated radicals can, if appropriate, contain 1 to 3 identical or different substituents from the group comprising alkyl (1 to 20 carbon atoms), alkenyl (2 to 20 carbon atoms), alkinyl (7 to 20 C atoms), alkoxy (1 to 20 C atoms), fluorine, chlorine, bromine, iodine, trifluoromethyl, monofluoroalkoxy (1 to 10 C atoms), polyfluoroalkoxy (1 to 10 C atoms), hydroxyl, amino, monoalkylamino (1 to 10 C atoms), dialkylamino (1 to 10 C atoms), nitro, cyano, azido, carboxyl, carbalkoxy ($C_1$-$C_{10}$), carboxamido, sulphonamido, $SO_m$-alkyl (m=0 to 2, 1 to 20 C atoms) phenyl, benzyl, benzyloxy or benzylthio, it being possible for the 4 last-mentioned substituents to contain, if appropriate, 1 to 3 radicals from the group comprising alkyl (1 to 5 C atoms), alkoxy (1 to 5 C atoms), alkylthio (1 to 5 C atoms), fluorine, chlorine, bromine, iodine, cyano, nitro, azido, hydroxyl, trifluoromethyl, amino, alkylamino (1 to 6 C) atoms or dialkylamino (1 to 6 C atoms), $R^1$ represents a straight-chain, branched or cyclic saturated or unsaturated hydrocabon radical (1 to 20 C atoms) which can, if appropriate, be interrupted in the chain by 1 or 2 oxygen or sulphur atoms and can be optionally substituted by one or more fluorine atoms, $NO_2$, trialkylsilyl (3 to 12 C atoms), hydroxyl, chlorine, bromine, iodine or cyano, $R^2$ represents hydrogen, —$NH_2$, —CHO, cyano, —$CH_2OH$ or a straight-chain or branched saturated or unsaturated hydrocarbon radical (1 to 8 C atoms) and $R^3$ represents hydrogen or a straight-chain or branched alkyl radical (1 to 10 C atoms) which is, if appropriate, interrupted in the alkyl chain by one or two oxygen atoms and can be optionally substituted by fluorine, chlorine, bromine, iodine, —CN, —$NH_2$, —OH or morpholino, in the form of isomers, isomer mixtures, racemates and optical antipodes.

Of particular interest are compounds of the general formula (I), in which

R represents a phenyl, naphthyl, thienyl, pyrryl, imidazolyl, oxazolyl, isoxazolyl, thiazolyl, pyridyl, pyridazinyl, pyrimidyl, quinolyl, isoquinolyl, indolyl, benzimidazolyl, quinazolyl, thionaphthenyl, chromonyl, thiochromonyl, chromenyl, thiochromenyl, benzoxadiazolyl or benzthiadiazolyl radical, and the stated radical can, if appropriate, contain 1 to 3 identical or different substituents from the group comprising alkyl (1 to 15 carbon atoms), alkenyl (2 to 15 carbon atoms), alkinyl (2 to 15 C atoms), alkoxy (1 to 15 C atoms), fluorine, chlorine, bromine, iodine, trifluoromethyl, monofluoroalkoxy (1 to 5 C atoms), polyfluoroalkoxy (1 to 5 C atoms), hydroxyl, amino, monoalkylamino (1 to 5 C atoms), dialkylamino, (1 to 5 C atoms), nitro, cyano, azido, carboxyl, carboxamido, sulphonamido, $SO_m$-alkyl (m=0 to 2, 1 to 10 C atoms), phenyl, benzyl, benzyloxy or benzylthio, it being possible for the 4 last-mentioned substituents to contain, if appropriate, 1 to 3 radicals from the group comprising alkyl (1 to 4 C atoms), alkoxy (1 to 4 C atoms), alkylthio (1 to 4 C atoms), fluorine, chlorine, cyano, nitro, hydroxyl, trifluoromethyl, amino, alkylamino (1 to 4 C atoms) or dialkylamino (1 to 4 C atoms).

$R^1$ represents a straight-chain, branched or cyclic saturated or unsaturated hydrocarbon radical (1 to 15 C atoms) which can, if appropriate, be interrupted in the chain by 1 or 2 oxygen or sulphur atoms and can be optionally substituted by one or more fluorine atoms, $NO_2$, trialkylsilyl (3 to 9 C atoms), hydroxyl, chlorine, or cyano, $R^2$ represents hydrogen, —CHO, —cyano or a straight-chain or branched saturated or unsaturated hydrocarbon radical (1 to 6 C atoms) and $R^3$ represents hydrogen or a straight-chain or branched alkyl radical (1 to 6 C atoms) which is, if appropriate, interrupted in the alkyl chain by one or two oxygen atoms and can be optionally substituted by fluorine, chlorine, cyano, hydroxyl or morpholino.

Compounds which may be mentioned preferably are those of the general formula (I) in which R represents a phenyl, naphthyl, pyridyl or thiochromenyl radical, and the stated radical can, if appropriate, contain 1 or 2 identical or different substituents from the group comprising alkyl (1 to 5 carbon atoms), alkoxy (1 to 5 C atoms), chlorine, trifluoromethyl, difluoroalkoxy (1 to 5 C atoms), nitro, cyano, azido, $SO_m$-alkyl (m=0 to 2, 1 to 5 C atoms) and phenyl, it being possible for the last-mentioned phenyl radical to contain, if appropriate, 1 or 2 radicals from the group comprising alkyl (1 to 3 C atoms), alkoxy (1 to 3 C atoms), fluorine, chlorine and trifluoromethyl, $R^1$ represents a straight-chain or branched alkyl radical (1 to 5 C atoms) which can, if appropriate, be interrupted in the chain by an oxygen or sulphur atom and can be optionally substituted by one or more fluorine atoms, or trialkylsilyl (3 to 6 C atoms), $R^2$ represents hydrogen or a straight-chain or branched alkyl radical (1 to 4 C atoms), and $R^3$ represents hydrogen or a straight-chain or branched alkyl radical (1 to 4 C atoms) which is, if appropriate, interrupted in the alkyl chain by an oxygen atom and can be optionally substituted by morpholino.

The compounds according to the invention, of the general formula (I), can be prepared by a process in which benzylidene compounds of the general formula (II)

in which

R has the meaning give above, are reacted with enamines of the general formula (III)

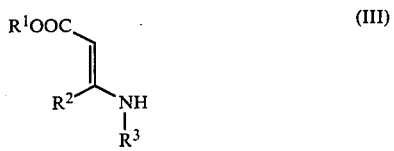

in which $R^1$, $R^2$ and $R^3$ have the meanings given above, if appropriate in the presence of inert organic solvents at temperatures between 0° and 150°.

The reactants can be used in any desired ratios; equimolar amounts are preferably used, but (III) can be employed in up to five-fold excess.

The reaction temperature is preferably 20° to 60° C. when the reaction is carried out in the presence of inert solvents, and 40° to 140° C. when the reaction is carried out without solvents.

Suitable solvents are all inert solvents, such as, for example, alcohols, preferably tert.-butanol, or aromatics, such as toluene or benzene.

Benzylidene compounds (II) used for the preparation are known and can be prepared by known processes (J. Org. Chem. 43, 1541 (1978) and Z. Chem. 10, 341 (1970)).

Aminocrotonates (III) used as starting materials are known and can be prepared by known processes (Cope, J. Amer. Chem. Soc. 67, 1017 (1945)).

The compounds (I) according to the invention eliminate water in weakly acidic solution and, after oral administration, are therefore converted to the 1,4-dihydropyridinelactones (IV), which may be the compounds which are actually effective.

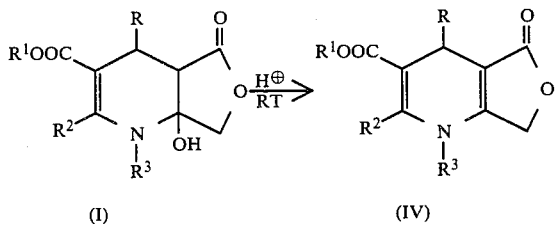

Suitable solvents for converting (I) to (IV) are all inert solvents, such as, for example, alcohols, for example ethanol, aromatics, such as toluene, or esters, such as ethyl acetate.

Suitable catalysts are all mineral acids, such as, for example, hydrochloric acid or sulphuric acid.

The reaction temperature is $-30°$ to the boiling point of the solvent, preferably 0° to $+50°$ C.

Like the compounds IV already described, the compounds according to the invention exhibit a valuable pharmacological action spectrum. They can be used as cardiotonics for improving the contractility of the heart. Moreover, they increase the flow of $Ca^{++}$ into the cells and therefore be employed as antihypotonics, for lowering the blood sugar level, for reducing the swelling of mucous membranes and for influencing the salt balance and/or fluid balance.

The compounds according to the invention can be converted in a known manner to the customary formulations, such as tablets, capsules, dragees, pills, granules, aerosols, syrups, emulsions, suspensions and solutions, using inert, non-toxic, pharmaceutically suitable excipients or solvents. The therapeutically active compound should be present in a concentration of about 0.5 to 90% by weight of the total mixture, that is to say in amounts which suffice to achieve the stated dosage range.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid excipients, such as, for example, natural rock powders (for example kaolins, aluminas, talc chalk), synthetic rock powders (for example highly disperse silica and silicates), sugars (for example cane sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is preferably oral. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be concomitantly used when making tablets. In the case of aqueous suspensions and/or elixirs, the active compounds can be mixed with various flavor-improving agents or colorants in addition to the abovementioned auxiliary substances.

In order to achieve effective results, in general it has proved advantageous to administer a dose of about 0.01 to 20 mg/kg, preferably 0.1 to 10 mg/kg, more preferably 1 to 5 mg/kg of body weight per day.

Nevertheless, it can at times be necessary to deviate from the amounts mentioned, and in particular to do so as a function of the body weight of the experimental animal and of the nature of the administration method, but also because of the species of animal and its individual behavior towards the medicament, and the nature of the formulation of the medicament and the time or interval over which the administration takes place. Thus, it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. The general sense of the above statements also applies in this case.

EXAMPLE 1

Methyl 7a-hydroxy-2-methyl-4-(3-nitrophenyl)-5-oxo-1,4,4a,5,6,7a-hexahydrofuro[3,4-b]pyridine-3-carboxylate.

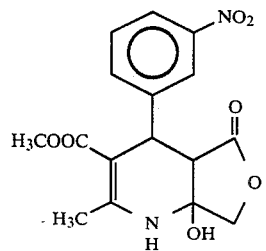

4 mmol of 3-(3-nitrobenzylidene)-4-oxo-butyrolactone (E/Z mixture) and 4.4 mmol of methyl 3-aminocrotonate are suspended in 5 g of tert.-butanol, and the suspension is stirred for 3 hours at 30° C. It is evaporated down at room temperature in a rotary evaporator, and the residue is crystallized with a small amount of methanol. M.p.: 147°–149° C. (from methanol):

EXAMPLE 2

Methyl 7a-hydroxy-2-methyl-4-(2-nitrophenyl)-5-oxo-1,4,4a,5,6,7a-hexahydrofuro[3,4-b]pyridine-3-carboxylate

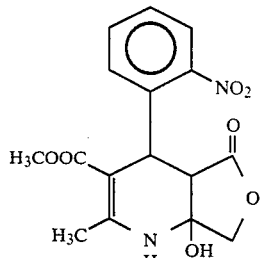

2 mmol of 3-(2-nitrobenzylidene)-4-oxo-butyrolactone (E/Z mixture) and 4 mmol of methyl-3-aminocrotonate are mixed, and the mixture is heated to 90° C. for 1 hour. Methanol is added, and the product is filtered off under suction. M.p.: 163° C. (decomposition).

EXAMPLE 3

Ethyl 7a-hydroxy-2-methyl-4-(2-nitrophenyl)-5-oxo-1,4,4a,5,7,7a-hexahydrofuro[3,4-b]pyridine-3-carboxylate

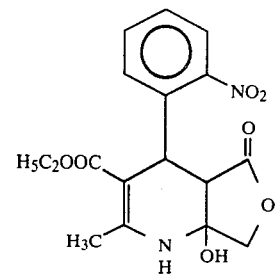

Preparation analogous to Example 2. M.p.: 160°–161° C. (decomposition).

EXAMPLE 4

Ethyl 7a-hydroxy-2-methyl-4-(3-nitrophenyl)-5-oxo-1,4,4a,5,6,7a-hexahydrofuro[3,4-b]pyridine-3-carboxylate

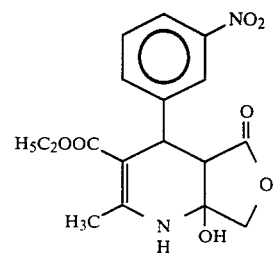

Preparation analogous to Example 1, but with a reaction time of 4 hours. M.p.: 147° C.

EXAMPLE 5

Ethyl 7a-hydroxy-2-methyl-4-(2-methylphenyl)-5-oxo-1,4,4a,5,7,7a-hexahydrofuro[3,4-b]pyridine-3-carboxylate

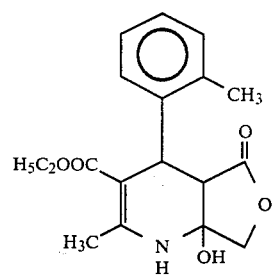

Preparation analogous to Example 1, reaction temperature: 30° C., reaction time: overnight. M.p.: 116°–118° C.

CONVERSION TO 1,4-DIHYDROPYRIDINES

EXAMPLE 6

Ethyl 2-methyl-4-(2-methylphenyl)-5-oxo-1,4,5,7-tetrahydrofuro[3,4-b]pyridine-3-carboxylate

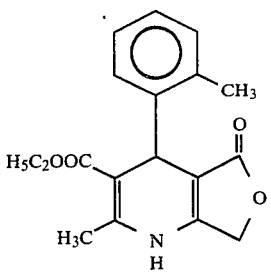

Ethyl 7a-hydroxy-2-methyl-4-(2-methylphenyl)-5-oxo-1,4,4a,5,7,7a-hexahydrofuro[3,4-b]pyridine-3-carboxylate is dissolved in ethanol and one drop of ethanolic HCl is added, after which the mixture is evaporated down. M.p.: 196°–198° C.

EXAMPLE 7

Ethyl 2-methyl-4-(3-nitrophenyl)-5-oxo-1,4,5,7-tetrahydrofuro[3,4-b]pyridine-3-carboxylate

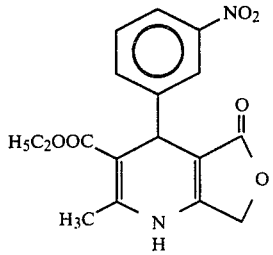

Ethyl 7a-hydroxy-2-methyl-4-(3-nitrophenyl)-5-oxo-1,4,4a,5,7,7a-hexahydrofuro[3,4-b]pyridine-3-carboxylate is dissolved in toluene, catalytic amounts of p-toluenesulphonic acid are added, the mixture is warmed for a short time and extracted by shaking with $Na_2CO_3$ solution, and the organic phase is dried and evaporated down. M.p.: 229° C.

It will be appreciated that the instant specification and examples are set forth by way of illustration and not limitation, and that various modifications and changes may be made without departing from the spirit and scope of the present invention.

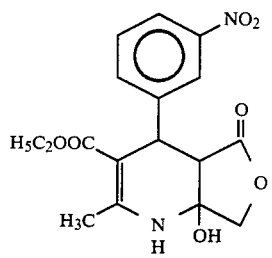

We claim:

1. A hydroxytetrahydropyridinelactone of the formula

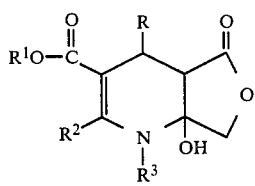

in which

R represents a phenyl or naphthyl radical, and the stated radicals may carry 1 or 2 identical or different substituents from the group consisting of $C_1$-$C_5$-alkyl, $C_1$-$C_5$-alkoxy, chlorine, trifluoromethyl, difluoro-$C_1$-$C_5$-alkoxy, nitro, cyano, azido, $SO_m$-alkyl (m=0 to 2, 1 to 5 C atoms) and phenyl, it being possible for the last-mentioned phenyl radical to carry 1 or 2 radicals from the group comprising $C_1$-$C_3$-alkyl, $C_1$-$C_3$-alkoxy, fluorine, chlorine and trifluoromethyl, $R^1$ represents a straight-chain or branched $C_1$-$C_5$-alkyl radical which may be interrupted in the chain by an oxygen or sulphur atom and may be optionally substituted by one or more fluorine atoms or $C_3$-$C_6$-trialkylsilyl, $R^2$ represents hydrogen or a straight-chain or branched $C_1$-$C_4$-alkyl radical, and $R^3$ represents hydrogen or a straight-chain or branched $C_1$-$C_4$-alkyl radical which may be interrupted in the alkyl chain by an oxygen and may be optionally substituted by morpholino.

2. A compound according to claim 1 wherein such compound is methyl 7a-hydroxy-2-methyl-4-(3-nitrophenyl)-5-oxo-1,4,4a,5,6,7a-hexahydrofuro[3,4-b]pyridine-3-carboxylate of the formula

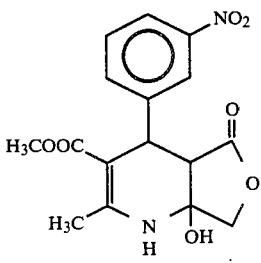

3. A compound according to claim 1 wherein such compound is methyl 7a-hydroxy-2-methyl-4-(2-nitrophenyl)-5-oxo-1,4,4a,5,6,7a-hexahydrofuro[3,4-b]pyridine-3-carboxylate of the formula

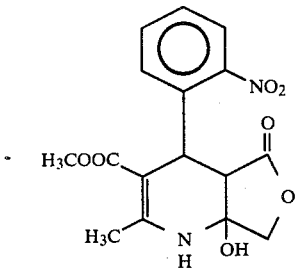

4. A compound according to claim 1 wherein such compound is ethyl 7a-hydroxy-2-methyl-4-(2-nitrophenyl)-5-oxo-1,4,4a,5,7,7a-hexahydrofuro[3,4-b]pyridine-3-carboxylate of the formula

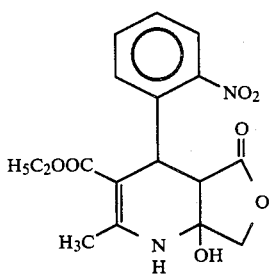

5. A compound according to claim 1 wherein such compound is ethyl 7a-hydroxy-2-methyl-4-(3-nitrophenyl)-5-oxo-1,4,4a,5,6,7a-hexahydrofuro[3,4-b]pyridine-3-carboxylate of the formula 6. A compound according to claim 1 wherein such compound is ethyl 7a-hydroxy-2-methyl-4-(2-methylphenyl)-5-oxo-1,4,4a,5,7,7a-hexahydrofuro[3,4-b]pyridine-3-carboxylate of the formula

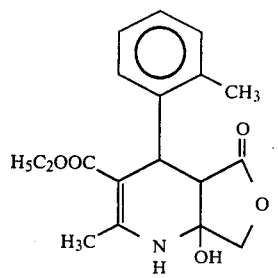

7. An antihypotonic composition comprising an amount of a compound according to claim 1 effective therefor and a diluent.

8. A unit dose of a composition according to claim 7 in the form of a tablet, capsule or ampule.

9. A method of raising the blood pressure of a patient which comprises administering to such patient an amount effective therefor of a compound according to claim 1.

10. The method according to claim 9, wherein such compound is methyl 7a-hydroxy-2-methyl-4-(3-nitrophenyl)-5-oxo-1,4,4a,5,6,7a-hexahydrofuro[3,4-b]pyridine-3-carboxylate, methyl 7a-hydroxy-2-methyl-4-(2-nitrophenyl)-5-oxo-1,4,4a,5,6,7a-hexahydrofluoro[3,4-b]pyridine-3-carboxylate, ethyl 7a-hydroxy-2-methyl-4-(2-nitrophenyl)-5-oxo-1,4,4a,5,7,7a-hexahydrofuro[3,4-b]pyridine-3-carboxylate, ethyl 7a-hydroxy-2-methyl-4-(3-nitrophenyl)-5-oxo-1,4,4a,5,6,7a-hexahydrofuro[3,4-b]pyridine-3-carboxylate, or ethyl 7a-hydroxy-2-methyl-4-(2-methylphenyl)-5-oxo-1,4,4a,5,7,7a-hexahydrofuro[3,4-b]pyridine-3-carboxylate.

* * * * *